United States Patent [19]

Mauldin et al.

[11] Patent Number: 4,556,752

[45] Date of Patent: Dec. 3, 1985

[54] PREPARATION OF LIQUID HYDROCARBONS FROM METHANOL

[75] Inventors: Charles H. Mauldin; Virgil L. Payne, both of Baton Rouge, La.

[73] Assignee: Exxon Research and Engineering Co., Florham Park, N.J.

[21] Appl. No.: 626,026

[22] Filed: Jun. 29, 1984

[51] Int. Cl.$^4$ ................................................ C07C 1/00
[52] U.S. Cl. .................................. 585/640; 585/639; 585/733; 585/469
[58] Field of Search ................. 585/640, 639, 733, 469

[56] References Cited

U.S. PATENT DOCUMENTS

| | | |
|---|---|---|
| 4,088,671 | 5/1973 | Kebylinaki . |
| 4,338,089 | 7/1982 | Schaper et al. . |
| 4,373,109 | 2/1983 | Olah ........................... 585/640 |
| 4,385,193 | 5/1983 | Bijwaard et al. . |
| 4,423,274 | 12/1983 | Daviduk et al. ............ 585/640 |
| 4,465,889 | 8/1984 | Anthony et al. ........... 585/733 |

FOREIGN PATENT DOCUMENTS 2073237 10/1981 United Kingdom .

OTHER PUBLICATIONS

Kikuchi et al, "Fischer-Tropsch Synthesis of Hydrocarbons over Ruthenium Supported on Transition Metal Oxide, Pan-Pacific Synfuels Conf., vol. 1, Nov. 17-19, 1982, Tokyo.

Kikuchi et al, "Fischer-Tropsch Synthesis over Titania-Supported Ruthenium Catalysts", Applied Catalysis, Oct. 1984, pp. 251-260.

Primary Examiner—D. E. Gantz
Assistant Examiner—Chung K. Pak
Attorney, Agent, or Firm—Llewellyn A. Proctor

[57] ABSTRACT

A process for the preparation of liquid hydrocarbons from methanol by conversion of the methanol over a cobalt-titania catalyst, especially a thoria promoted cobalt-titania catalyst, particularly a cobalt-titania or cobalt-thoria-titania catalyst having a rutile:anatase weight ratio of at least 2:3. The methanol is contacted, preferably with added hydrogen, over said catalyst to produce, at reaction conditions, an admixture of $C_{10}+$ linear paraffins and olefins, which can be further refined to high quality middle distillate fuels, and other valuable products such as mogas, diesel fuel, jet fuel, lubes and speciality solvents, especially premium middle distillate fuels of carbon number ranging from about $C_{10}$ to about $C_{20}$.

14 Claims, No Drawings

PREPARATION OF LIQUID HYDROCARBONS FROM METHANOL

BACKGROUND AND PROBLEMS

I. Field of the Invention

This invention relates to a process for the preparation of liquid hydrocarbons from methanol. In particular, it relates to a process wherein $C_{10}+$ distillate fuels, and other valuable products are prepared by reaction of methanol, and preferably hydrogen, over certain types of cobalt catalysts.

II. The Prior Art

Methane is often available in large quantities from process streams either as an undesirable by-product in admixture with other gases, or as an off gas component of a process unit, or units. More importantly, however, methane is the principle component of natural gas, and it is produced in considerable quantities in oil and gas fields. The existence of large methane, natural gas reserves coupled with the need to produce premium grade transportation fuels, particularly middle distillate fuels, creates a large incentive for the development of a new gas-to-liquids process. Conventional technology, however, is not entirely adequate for such purpose. Nonetheless, technology is available for the conversion of synthesis gas, which can be obtained from coal or natural gas, to produce methanol, a product of currently limited marketability. However, to utilize the existing technology, there is a need for a process, and catalysts, suitable for conversion of methanol to high quality transportation fuels, particularly middle distillate fuels.

Objects

It is, accordingly, a primary objective of the present invention to supply this need.

A particular object is to provide a novel process utilizing said catalyst compositions for the conversion of methanol to admixtures of $C_{10}+$ linear paraffins and olefins which can be further refined and upgraded to high quality middle distillate fuels, and other valuable products.

A particular object is to provide a process as characterized, useful in combination with an upstream conventional methanol synthesis plant.

The Invention

These objects and others are achieved in accordance with the present invention embodying a process wherein methanol is contacted, preferably with hydrogen, over a cobalt-titania catalyst, especially a thoria promoted cobalt-titania catalyst, particularly a cobalt-titania or cobalt-thoria-titania catalyst having a rutile:anatase weight ratio of at least 2:3, to produce, at reaction conditions, an admixture of $C_{10}+$ linear paraffins and olefins, which can be further refined to high quality middle distillate fuels, and other valuable products such as mogas, diesel fuel, jet fuel, lubes and speciality solvents, especially premium middle distillate fuels of carbon number ranging from about $C_{10}$ to about $C_{20}$.

The cobalt-titania catalyst, or thoria promoted cobalt-titania catalyst, is one which consists essentially of cobalt, or cobalt and thoria, composited, or dispersed upon titania ($TiO_2$), or a titania-containing carrier, or support. A preferred, and more selective catalyst for use in methanol conversion reactions is one containing titania wherein the rutile:anatase weight ratio ranges from about 2:3 to about 3:2. This ratio is determined in accordance with ASTMD 3720-78: Standard Test Method for *Ratio of Anatase to Rutile in Titanium Dioxide Pigments by Use of X-Ray Diffraction.* The cobalt, or cobalt and thoria, is dispersed on the support in catalytically effective amounts. Suitably, in terms of absolute concentration, the cobalt is dispersed on the support in amounts ranging from about 2 percent to about 25 percent, preferably from about 5 percent to about 15 percent, based on the total weight of the catalyst composition (dry basis). The thoria is dispersed on the support in amounts ranging from about 0.1 percent to about 10 percent, preferably from about 0.5 percent to about 5 percent, based on the total weight of the catalyst composition (dry basis). Suitably, the thoria promoted cobalt catalyst contains thoria, $ThO_2$, and cobalt, Co, in ratio of Co:$ThO_2$ ranging from about 1:1 to about 20:1, preferably from about 2:1 to about 15:1, based on the weight of the total amount of $ThO_2$ and Co contained on the catalyst. These catalyst compositions, it has been found, produce at reaction conditions a product which is predominantely $C_{10}+$ linear paraffins and olefins, with very little oxygenates. These catalysts provide high selectivity, high activity and good activity maintenance in the conversion of methanol to $C_{10}+$ hydrocarbons.

In conducting the reaction the partial pressure of methanol within the reaction mixture is generally maintained above about 100 pounds per square inch absolute (psia), and preferably above about 200 psia. It is preferable to conduct the methanol reaction in the presence of some hydrogen. The hydrogen may be added or generated in situ. Suitably methanol, and hydrogen, are employed in molar ratio of $CH_3OH:H_2$ above about 2:1 and preferably above 8:1, to increase the concentration of $C_{10}+$ hydrocarbons in the product. Suitably, the $CH_3OH:H_2$ molar ratio, where hydrogen is employed, ranges from about 2:1 to about 60:1, and preferably the methanol and hydrogen are employed in molar ratio ranging from about 8:1 to about 30:1. Inlet hydrogen partial pressures preferably range below about 80 psia, and more preferably below about 40 psia. When hydrogen is added, inlet hydrogen partial pressures preferably range from about 5 psia to about 80 psia, and more preferably from about 10 psia to about 40 psia. In general, the reaction is carried out at liquid hourly space velocities ranging from about 0.1 $hr^{-1}$ to about 10 $hr^{-1}$, preferably from about 0.2 $hr^{-1}$ to about 2 $hr^{-1}$, and at temperatures ranging from about 150° C. to about 350° C., preferably from about 180° C. to about 250° C. Methanol partial pressures preferably range from about 100 psia to about 1000 psia, more preferably from about 200 psia to about 700 psia. The product generally and preferably contains 60 percent, or greater, and more preferably 75 percent, or greater, $C_{10}+$ liquid hydrocarbons which boil above 160° C. (320° F.).

Cobalt-titania, and especially thoria promoted cobalt-titania catalysts exhibit high activity and selectivity in the conversion of a feed consisting essentially of methanol, and hydrogen, to $C_{10}+$ hydrocarbons. The catalysts employed in the practice of this invention are prepared by techniques known in the art for the preparation of these and other catalysts. The catalyst can, e.g., be prepared by gellation, or cogellation techniques. Suitably, however, cobalt can be composited alone, or with the thoria, upon a previously pilled, pelleted, beaded, extruded, or sieved titania or titania-containing support material by the impregnation method. In preparing catalysts, the metal, or metals, is deposited from solution on the support to provide the desired absolute amount of the metal, or metals. Suitably, the cobalt is composited with the support by contacting the support with a solution of a cobalt-containing compound, or salt, e.g., a nitrate, carbonate or the like. The thoria, where thoria is to be added, can then be composited with the support in similar manner, or the thoria can first be impregnated upon the support, followed by impregnation upon the support of the cobalt. Optionally, the thoria and cobalt cn be co-impregnated upon the support. The cobalt compounds used in the impregnation can be any organometallic or inorganic compound which decomposes to give cobalt oxide upon calcination, such as cobalt nitrate, acetate, acetylacetonate, naphthenate, carbonyl, or the like. Cobalt nitrate is especially preferred while cobalt halide and sulfate salts should generally be avoided. The salts may be dissolved in a suitable solvent, e.g., water, or an organic solvent, e.g., a hydrocarbon such as acetone, methanol, pentane or the like. The amount of impregnation solution used should be sufficient to completely immerse the carrier, usually within the range from about 1 to 20 times the carrier by volume, depending on the concentration of the cobalt-containing compound in the impregnation solution. The impregnation treatment can be carried out under a wide range of conditions including ambient or elevated temperatures. Metal components other than ruthenium may also be added as promoters. Exemplary of such promoters are nickel, platinum, palladium, rhodium and lanthanium. In general, however, the addition of these metals have not been found to provide any significant benefit. In fact, surprisingly, the addition of copper and iron appear to have had a somewhat adverse effect upon the reaction. For this reason, the preferred catalyst is one which consists essentially of cobalt, or cobalt and thoria, dispersed upon the titania, or titania-containing support; or, in other words, catalysts which do not contain a significant amount of a metal, or metals, other than cobalt, or metals other than cobalt and thoria, dispersed upon the titania or titania-containing support.

The catalyst, after impregnation, is dried by heating at a temperature between about 30° C. and about 75° C. in the presence of nitrogen or oxygen, or both, in an air stream or under vacuum. The catalyst can be calcined in air at a temperature between about 75° C. and about 500° C., preferably between about 200° C. and about 300° C. The metal, or metals, contained on the catalyst can then be reduced and thereby activated. It is necessary to activate the catalyst prior to use. Reduction of the metal, or metals, is performed by contact of the catalyst with hydrogen or a hydrogen-containing gas stream at temperatures above about 200° C.; preferably above about 250° C. Suitably, the catalyst is reduced at temperatures ranging from about 250° C. to about 500° C. over periods ranging from about 0.5 to about 24 hours at pressures ranging from ambient to about 40 atmospheres. A gas containing hydrogen and inert components, or a gas containing hydrogen and carbon dioxide in admixture are satisfactory for use in carrying out the reduction.

The invention will be more fully understood by reference to the following demonstrations and examples which present comparative data illustrating its more salient features.

The data given in the examples which follow were obtained in a small fixed bed reactor unit, conventional material balance work-up and analytical data having been obtained during the runs which were conducted over various periods. All parts are in terms of weight units except as otherwise specified. Feed compositions are expressed as molar ratios of the components.

The "Schulz-Flory Alpha" is a known method for describing the product distribution in Fischer-Tropsch synthesis reactions, and it is also useful in describing the product distribution from methanol conversion reactions. The Schulz-Flory Alpha is the ratio of the rate of chain propagation to the rate of propagation plus termination, and is described from the plot of $\ln(W_n/n)$ versus n, where $W_n$ is the weight fraction of product with a carbon number of n. In the examples below, an Alpha value was derived from the $C_{10}/C_{20}$ portion of the product. The Alpha value is thus indicative of the selectivity of the catalyst for producing heavy hydrocarbons from the methanol, and is indicative of the approximate amount of $C_{10}+$ hydrocarbons in the product. For example, a Schulz-Flory Alpha of 0.80 corresponds to about 35% by weight of $C_{10}+$ hydrocarbons in the product, a generally acceptable level of $C_{10}+$ hydrocarbons. A Schulz-Flory Alpha of 0.85, a preferred Alpha value, corresponds to about 54% by weight of $C_{10}+$ hydrocarbons in the products, and a Schulz-Flory Alpha of 0.90, a more preferred Alpha value, corresponds to about 74% by weight of $C_{10}+$ hydrocarbons in the product.

The cobalt-titania catalysts used in the examples below were prepared by the following procedure: Titania (Degussa P-25 $TiO_2$) was used as the support after mixing with sterotex, and after pilling, grinding, and screening to 16–20 mesh (Tyler). Two versions of $TiO_2$ were prepared by calcining portions of the $TiO_2$ in air at 500° C. and 600° C., respectively, overnight. This gave $TiO_2$ supports with the following properties:

| Calcination Temperature, °C. | Rutile:Anatase Ratio[1] | Surface Area $m^2/g$ | Pore Volume ml/g |
|---|---|---|---|
| 500 | 1.2 | 33–36 | 0.28–0.40 |
| 600 | >30:1 | 10–16 | 0.11–0.15 |

[1]ASTMD 3720-78: Standard Test Method for Ratio of Anatase to Rutile in Titanium Dioxide Pigments by use of X-Ray Diffraction.

Catalysts, of 16–20 mesh size, were prepared from selected portions of these materials by simple impregnation of the support with cobaltous nitrate, and in some cases with cobaltous nitrate and thorium nitrate, from acetone solution using a rotary evaporator, drying in a vacuum oven at 150° C., and calcining of the catalysts for three hours in flowing air in a quartz tube. The catalysts were charged to a reactor, reduced in $H_2$ at 450° C. for one hour, and then reacted with methanol at the conditions described in the examples.

In the example which immediately follows a series of runs were conducted with a thoria promoted cobalt-titania catalyst to demonstrate the effect of pressure, notably methanol partial pressure in converting methanol, and hydrogen, to hydrocarbons.

EXAMPLE 1

A feed constituting an admixture of methanol and hydrogen in varying molar ratios of $CH_3OH:H_2$ was contacted over a thoria promoted cobalt-titania catalyst (12% CO—2% $ThO_2$—$TiO_2$) at total pressures ranging from ambient to 600 pounds per square inch gauge, psig, methanol partial pressures ranging from 2 to 492 psia, at a temperature of 230° C. and at space velocities of 3500 GHSV and 500 GHSV, respectively. The feed was diluted in certain cases with carbon dioxide and argon (Ar); argon being added to maintain good operability in terms of obtaining acceptable material balances. Reference is made to Table I.

TABLE I

| | 12% Co—2% ThO$_2$—TiO$_2$ | | | | | |
|---|---|---|---|---|---|---|
| Pressure | | | | | | |
| Total, psig | 0 | 40 | 100 | 250 | 400 | 600 |
| CH$_3$OH partial, psia | 2 | 44 | 92 | 212 | 332 | 492 |
| Temperature, °C. | | | 230 | | | |
| Feed Composition | 1 CH$_3$OH: 5.7 H$_2$ | | 40 CH$_3$OH:2 H$_2$:1 CO$_2$:7 Ar | | | |
| GHSV, Hr.$^{-1}$ | 3500 | | | 500 | | |
| CH$_3$OH Conversion | 11 | 44 | 46 | 53 | 70 | 76 |
| Conversion rate g/hr/g × 10$^2$ | 8 | 23 | 24 | 28 | 37 | 40 |
| Carbon Product Distribution, Wt % | | | | | | |
| CO | 91.9 | 79.3 | 42.6 | 11.6 | 3.1 | 0.6 |
| CO$_2$ | 0.4 | 0.3 | 3.6 | 10.4 | 17.0 | 20.9 |
| CH$_4$ | 7.7 | 9.4 | 9.5 | 7.9 | 8.6 | 11.5 |
| C$_2$+ | — | 11.1 | 44.3 | 70.1 | 71.3 | 67.0 |

Inlet methanol partial pressures ranging above about 100 psia, and preferably above about 200 psia, it has been found are required to ensure optimum conversion of methanol to hydrocarbons. Low inlet methanol partial pressures favor conversion of methanol to only H$_2$ and CO with very little hydrocarbon production. The impact of pressure on conversion and selectivity are clearly illustrated in Table I. Inlet methanol partial pressures should range from about 100 psia to about 1000 psia, preferably from about 200 psia to about 700 psia. Total pressure will depend on the amount of H$_2$, CO$_2$, or other inerts present in the reaction mixture.

Low partial pressures of hydrogen are preferred in order to maximize the yield of the desired heavy hydrocarbons at the expense of light hydrocarbons. For cobalt-titania, and thorium promoted cobalt-titania catalysts, the preferred inlet hydrogen partial pressure is generally maintained below about 80 psia, and preferably below about 40 psia.

EXAMPLE 2

Example 1 was repeated utilizing both cobalt-thoria titania catalyst, and an unpromoted cobalt-titania catalyst, at 400 psig, GHSV=500, 40 CH$_3$OH:2H$_2$:1CO$_2$:7Ar. Reference is made to Table II. As shown in the table, the selectivity to heavy hydrocarbons is particularly high, especially at low temperature.

TABLE II

| 400 psig, GHSV = 500, 40 CH$_3$OH:2 H$_2$:1 CO$_2$:7 Ar | | |
|---|---|---|
| Catalyst | 12% Co—2% ThO$_2$—TiO$_2$ | 12% Co—TiO$_2$ |
| Temperature, °C. | 200        230 | 230 |
| CH$_3$OH Conversion, 35 hr | 30        70 | 52 |
| Carbon Product Distribution, Wt. % | | |
| CO | 2.8        3.1 | 5.5 |
| CO$_2$ | 7.2        17.0 | 12.9 |
| Dimethyl ether | 0.4        0.3 | 0.2 |
| CH$_4$ | 4.2        8.6 | 11.2 |
| CH$_2$+ | 85.4        71.0 | 70.2 |
| Wt. % CH$_4$ in hydrocarbon | 4.7        10.8 | 13.8 |
| Schulz-Flory Alpha | 0.92        0.88 | 0.86 |

From the values given for the Schulz-Flory Alpha, it is apparent that the conversion of the methanol to heavy hydrocarbons, and the selectivity of the catalysts for producing C$_{10}$+ hydrocarbons are quite high. The Co-TiO$_2$ catalyst produces about 58% by weight C$_{10}$+ hydrocarbons in the product, and the ThO$_2$ promoted Co-TiO$_2$ catalyst produces a product containing approximately 65% by weight and 80% by weight C$_{10}$+ hydrocarbons, at 230° C. and 200° C., respectively.

EXAMPLE 3

The product made from the Co-ThO$_2$-TiO$_2$ catalysts consists predominately of linear olefins and paraffins with a small amount of branched paraffins and olefins. Reference is made to Table III which shows the distribution of compounds within the C$_8$ fraction obtained by reaction of the methanol, and hydrogen, over the (12% Co—1% ThO$_2$—TiO$_2$), after 35 hours, at 230° C., 400 psig, GHSV=500 and 40 CH$_3$OH:2H$_2$:1CO$_2$7 Ar.

TABLE III

| Component in C$_8$ | Wt. % |
|---|---|
| n-octane | 78.2 |
| 1-octene | 0.6 |
| 4-octenes | 6.5 |
| 2-methylheptane | 4.8 |
| 3-methylheptane | 6.9 |
| 4-methylheptane | 3.0 |

Hydrogen in relatively small amount, as earlier suggested, is desirable to promote conversion of the methanol to hydrocarbons. The absolute hydrogen concentration is also of importance in promoting conversion, selectivity and yield in the production of the C$_{10}$+ hydrocarbons from methanol. Partial pressures less than about 80 psia are preferred, and more preferably less than 40 psia, in order to produce the higher molecular weight liquid hydrocarbons. H$_2$ partial pressures above about 80 psia, or even 40 psia, favor a lighter, more paraffinic product.

EXAMPLE 4

An admixture constituted of methanol and argon to which hydrogen was added in varying concentrations was passed into a reactor charged with a thoria promoted cobalt-titania catalyst, at 230° C., CH$_3$OH=332 psia, argon (83—$H_2$ psia) and GHSV=500. Measurements were made of the $CH_3OH$ conversion, and carbon product distribution in terms of weight percent hydrocarbons, carbon monoxide, carbon dioxide and dimethyl ether (DME) formation. The results are given in Table IV.

TABLE IV

| 230° C., $CH_3OH$ = 332 psia, Argon (83-$H_2$ psia), GHSV = 500 | | | |
|---|---|---|---|
| Inlet $H_2$ Partial Pressure psia | 0 | 17 | 83 |
| $CH_3OH$ Conversion, Wt. % | 38 | 52 | 83 |
| Carbon Product Distribution, Wt % | | | |
| CO | 8.5 | 3.9 | 0.9 |
| $CO_2$ | 11.3 | 8.9 | 12.2 |
| DME | 1.0 | 0.4 | 0.1 |
| $CH_4$ | 4.6 | 5.7 | 15.9 |
| $C_2$+ | 74.6 | 81.1 | 70.9 |
| Wt. % $CH_4$ in Hydrocarbon | 5.8 | 6.6 | 18.3 |

The addition of hydrogen to the reactor, it will be observed, increases the amount of methanol conversion. A hydrogen inlet pressure of 17 psia thus raises the conversion of the methanol by 14 percent (52%–38%), and the conversion of $C_2$+ hydrocarbons is increased by 6.5 percent (81.1%–74.6%). Increasing the inlet hydrogen partial pressure to 83 psia raises the amount of methanol conversion an additional 31 percent, viz., from 52 wt. % to 83 wt. %. However, $C_2$+ hydrocarbon selectivity is decreased somewhat, i.e., from 81.1 wt. % to 70.9 wt. %. Moreover, the hydrocarbon product is somewhat lighter, as indicated by the higher methane, and a Schulz-Flory Alpha of 0.82 is obtained.

EXAMPLE 5

A series of runs were made, at similar conditions, by contact of methanol with fixed beds of catalyst, as identified in Table V, contained in a stainless steel tube reactor. The runs were conducted at 230° C., 400 psig, GHSV=500 and 40 $CH_3OH$:2$H_2$:1$CO_2$:7Ar. Measurements were made of the $CH_3OH$ conversion with each of these catalysts, and analysis made of the wt. % carbon product distribution in terms of CO, $CO_2$, dimethyl ether, $CH_4$ and $C_2$+ hydrocarbons. The wt. % methane that was produced was also recorded. Reference is made to Table V.

TABLE V

| | | | | | | | |
|---|---|---|---|---|---|---|---|
| 230° C., 400 psig, GHSV = 500, 40 $CH_3OH$:2 $H_2$:1 $CO_2$:7 Ar | | | | | | | |
| Catalyst | $CH_3OH$ Conversion | Carbon Product Distribution, Wt. % | | | | | Wt. % $CH_4$ in Hydrocarbons |
| | | CO | $CO_2$ | DME | $CH_4$ | $C_2$+ | |
| 12% Co—2% $ThO_2$—$TiO_2$ | 70 | 2.9 | 12.6 | 0.5 | 7.4 | 76.6 | 8.8 |
| 100 Co:5 $ThO_2$: 8 MgO:200 Kieselguh[1] | 97 | 1.0 | 38.4 | — | 19.5 | 41.1 | 32.2 |
| 9 Co:1 Cu:2 $ThO_2$[2] | 20 | 16.7 | 42.4 | 0.2 | 5.2 | 35.5 | 12.8 |
| 12% Co—$SiO_2$ | 38 | 4.3 | 22.3 | 0.1 | 7.0 | 66.3 | 9.6 |
| 12% Co—$Al_2O_3$ | 64 | 2.8 | 21.8 | 2.4 | 9.9 | 63.1 | 13.6 |

[1]Prepared by procedure given at Page 137 and following; The Fischer-Tropsch and Related Synthesis, Storch, Golumbia and Anderson, John Willey and Sons, Inc., New York (1951).
[2]Shuma, K.; Morita, T.; Mujazaki Diagaku Kogakubu Kenkyu, 25, 19–24 (1979).

These data show that the thoria promoted cobalt-titania catalyst, as contrasted with prior art cobalt catalysts, is clearly the superior catalyst. It produces high conversion of the methanol (70 wt. %), and high production of $C_2$+ hydrocarbons (76.6 wt. %) with low methane in the carbon product distribution (8.8 wt. %). Whereas the 100 Co:5 $ThO_2$:8 MgO:200 Kieselguhr catalyst provides extremely high conversion of the methanol (97 wt. %), the production of $C_2$+ hydrocarbons (41.1 wt. %) is extremely low, and the production of $CO_2$ is unacceptably high (38.4 wt. %). Essentially one-third (32.2 wt. %) of the total hydrocarbons that are produced is methane. The methanol conversion level (20 wt. %) of the 9 Co:1 Cu:2 $ThO_2$, albeit a thoria promoted cobalt catalyst, is abysmal; and the $CO_2$ production level (42.4 wt. %) unacceptable. Only 35.5 wt. % of the carbon product distribution is hydrocarbons. The methanol conversion level of the 12% Co—$SiO_2$ (38 wt. %) is likewise poor, with fairly high production of $CO_2$ (22.3 wt. %). The 12% Co—$Al_2O_3$ catalyst, while superior to the 9 Co:1 Cu:2 $ThO_2$ and 12% Co—Si—$O_2$ catalysts, provides only 64 wt. % conversion of the methanol, with high production of $CO_2$ (21.8 wt. %). The $C_2$+ hydrocarbons product make is only 63.1 wt. % as compared with 76.6 wt. % for the 12% Co—2% $ThO_2$—$TiO_2$ catalyst.

EXAMPLE 6

The following data show the effect of different rutile contents on cobalt-titania catalysts used in the conversion of methanol to hydrocarbons. Thus, two 12% Co—$TiO_2$ catalysts, identical except that the $TiO_2$ base used to form one catalyst had a rutile:anatase weight ratio of 1.2:1, and the other a rutile:anatase weight ratio greater than 30:1, were used to convert methanol to hydrocarbons. The runs, made at identical conditions, were made at 230° C., 400 psig, GHSV=500 and 40 $CH_3OH$:2 $H_2$:1 $CO_2$:7 Ar. Reference is made to Table VI.

TABLE VI

| Effect of Rutile Content on 12% Co—$TiO_2$ Catalysts 230° C., 400 psig, GHSV = 500, 40 $CH_3OH$:2 $H_2$:1 $Co_2$:7 Ar | | |
|---|---|---|
| $TiO_2$ Properties | | |
| Rutile:Anatase Ratio, Wt. | 1.2:1 | >30:1 |
| Surface Area, $m^2/g$ | 36 | 10 |
| Pore Volume, ml/g | 0.30 | 0.11 |
| $CH_3OH$ Conversion | 66 | 100 |
| Carbon Product Distribution, Wt. % | | |
| CO | 2.6 | 0.8 |
| $CO_2$ | 15.6 | 27.8 |
| $CH_4$ | 9.0 | 17.1 |
| $C_2$+ | 72.8 | 54.3 |

These data clearly show that the catalyst which contains 1.2:1 ratio of rutile:anatase is the superior catalyst. Albeit the catalyst which contains a weight ratio of >30:1 rutile;anatase provides higher conversion, the methane gas make is almost double that of the other catalyst (17.1% vs. 9.0%), and the catalyst is far less selective in the production of $C_2$+ hydrocarbons (54.3% vs. 72.8%). Moreover, the catalyst which contains >30:1 rutile:anatase is more active in converting the methanol to carbon dioxide (27.8% vs. 15.6%).

The present process is admirably suitable for the conversion of methanol to hydrocarbons over cobalt-titania and thorium promoted cobalt-titania catalysts. The catalyst is constituted of cobalt or cobalt and thorium supported on $TiO_2$ or $TiO_2$-containing support containing such non-acidic materials as $SiO_2$, MgO, $ZnO_2$, $Al_2O_3$, or the like. The catalyst is preferably reduced with a H$_2$-containing gas at start-up. The reaction can be conducted in fixed bed, or slurry bed reactors with or without the recycle of any unconverted methanol, gas and/or liquid product.

It is apparent that various modifications and changes can be made without departing the spirit and scope of the present invention.

What is claimed is:

1. A process useful for the conversion of methanol to liquid hydrocarbons which comprises contacting a methanol feed at a methanol partial pressure of about 100 psia, and higher, over a catalyst which consists essentially of cobalt in amount ranging from about 2 percent to about 25 percent, or cobalt in amount ranging from about 2 percent to about 25 percent and thoria in amount ranging from about 0.1 percent to about 10 percent, based on the weight of the catalyst composition, composited with titania or a titania-containing support.

2. A process useful for the conversion of methanol to liquid hydrocarbons which comprises contacting an admixture of methanol and hydrogen, in methanol:hydrogen molar ratio equal to or greater than about 2:1 at a methanol partial pressure of about 100 psia, and higher, over a catalyst which consists essentially of cobalt, or cobalt and thoria in catalytically active amount composited with titania or a titania-containing support.

3. The process of claim 2 wherein the catalyst over which the admixture of methanol and hydrogen are reacted consists essentially of cobalt dispersed on the support, the catalyst containing from about 2 percent to about 25 percent cobalt, based on the weight of the catalyst composition.

4. The process of claim 3 wherein the catalyst contains from about 5 to about 15 percent cobalt, based on the weight of the catalyst composition.

5. The process of claim 2 wherein the catalyst over which the admixture of methanol and hydrogen are reacted consists essentially of cobalt and thoria dispersed on the support, the catalyst containing from about 2 percent to about 25 percent cobalt, and from about 0.1 percent to about 10 percent thoria, based on the total weight of the catalyst.

6. The process of claim 5 wherein the catalyst consists from about 5 percent to about 15 percent cobalt, and from about 0.5 percent to about 5 percent thoria.

7. The process of claim 2 wherein the molar ratio of methanol:hydrogen ranges from about 2:1 to about 60:1.

8. The process of claim 2 wherein the molar ratio of methanol:hydrogen ranges from about 8:1 to about 30:1.

9. The process of claim 2 wherein the methanol pressure ranges above about 200 psia.

10. The process of claim 2 wherein the methanol pressure ranges from about 200 psia to about 700 psia.

11. The process of claim 2 wherein the reaction conditions are defined within ranges as follows:
Methanol:H$_2$ ratio—about 2:1 to 60:1
Liquid Space Velocities, hr$^{-1}$—about 0.1 to 10
Temperatures, °C.—about 150 to 350
Methanol Partial Pressure, psia—about 100 to 1000.

12. The process of claim 2 wherein the reaction conditions are defined within ranges as follows:
Methanol:H$_2$ ratio—about 8:1 to 30:1
Liquid Space Velocities, hr$^{-1}$—about 0.2 to 2
Temperatures, °C.—about 180 to 250
Methanol Partial Pressure, psia—about 200 to 700.

13. The process of claim 2 wherein the titania of the titania or titania-containing support is one having a rutile:anatase weight ratio of at least 2:3.

14. The process of claim 2 wherein the titania of the titania or titania-containing support is one having a rutile:anatase weight ratio ranging from about 2:3 to about 3:2.

* * * * *